(12) United States Patent
Alroy

(10) Patent No.: US 7,680,602 B2
(45) Date of Patent: Mar. 16, 2010

(54) CONCEPTS AND METHODS FOR IDENTIFYING BRAIN CORRELATES OF ELEMENTARY MENTAL STATES

(76) Inventor: Daniel Alroy, 19 Stanten St., New York, NY (US) 10002

( * ) Notice: Subject to any disclaimer, the term of this patent is extended or adjusted under 35 U.S.C. 154(b) by 2029 days.

(21) Appl. No.: 09/871,560

(22) Filed: May 31, 2001

(65) Prior Publication Data

US 2002/0091654 A1    Jul. 11, 2002

(51) Int. Cl.
 *G01N 33/48* (2006.01)
(52) U.S. Cl. ........................................................ 702/19

(58) Field of Classification Search ................... 702/19; 364/413.05
See application file for complete search history.

(56) References Cited

U.S. PATENT DOCUMENTS 4,862,359 A * 8/1989 Trivedi et al. ............... 600/544

* cited by examiner

*Primary Examiner*—Jerry Lin

(57) ABSTRACT

Methods for identifying and modulating the subset of constitutively expressed locus-specific proteins in the brain, the deactivation of which selectively impairs the otherwise normal behavioral response to given stimulus, which is correlated with a particular elementary mental state.

1 Claim, No Drawings

CONCEPTS AND METHODS FOR IDENTIFYING BRAIN CORRELATES OF ELEMENTARY MENTAL STATES

CROSS-REFERENCES TO RELATED APPLICATIONS

Not applicable

STATEMENT REGARDING FEDERALLY SPONSORED RESEARCH

Not applicable

INCORPORATION-BY-REFERENCE OF MATERIAL SUBMITTED ON A COMPACT DISC

Not applicable

BACKGROUND OF THE INVENTION

Field of the Invention

The invention combines a conceptual discovery that the qualitative nature of elementary mental states is primarily determined by constitutively expressed locus-specific proteins in the brain, with means for their identification and modulation.

A BRIEF SUMMARY OF THE INVENTION

M. Summary, Objects and Advantages

M1 A conceptual discovery. The qualitative nature of an elementary mental state is primarily determined by the constitutively expressed locus-specific proteins of brain locus evoking it (K1 proteins).

M2 Methods. The invention provides methods for identifying brain loci, and of constitutively expressed proteins specific to said brain loci, the deactivation of either said loci, or said proteins, selectively impairs the otherwise normal behavioral response to said stimuli.

M3 Advantages. Identified said brain loci and said proteins provide the most selective targets for modulating the correlated elementary mental states, thus increasing the effectiveness, and decreasing the side-effects, of medical intervention.

DETAILED DESCRIPTION OF THE INVENTION

Background

Description of Prior Art

A. Some Fundamental Conceptual Issues

A1 The search for neural correlates of mental states. Mental states, though private, may be investigated through their physical manifestations in the brain. Hence the current search for identifying brain correlates of mental states (Chalmers 2001). However, the computer model of the brain implies that no mental state can have a unique brain correlate. To date, none have been found. It turns out that the implication of the computer model is empirically false, and that the technique necessary for identifying the brain correlates have been available for over a decade. The following briefly reviews basic conceptions that underlie present-day views about the relation of the mind to the brain.

A2 The central tenet underlying present-day notions about the nature of the mind. The great majority of neuroscientists take it for granted that sensations are received in the central nervous system (CNS) from the peripheral nervous system (PNS). This assumption is a manifestation of the tabula rasa doctrine that was introduced by John Locke (1775/1975). It denies that mental states are innate, or evoked in the CNS. Locke followed Democritus, Galileo, and Newton in partitioning what is perceived into properties such as size and shape, which were attributed to the external world, and properties such as sound and color, which were deemed to be subjective. This made Locke's version of the tabula rasa doctrine dualistic.

A3 Physicalism.

A3.1 Physicalism is a non-dualistic version of the tabula rasa doctrine. Physicalism removes the dualistic element of the tabula rasa doctrine by considering properties such as sound and color to be properties of the external world, and thus objective. Neuroscientists who subscribe to Physicalism take sound, for example, to be a property of air vibration (Kelley 1991). Similarly, color is taken to be a property of electromagnetic radiation.

A3.2 Physicalism denies that the mind makes a difference. Physicalism goes beyond the tabula rasa doctrine in asserting that the mind is causally inert. In a characteristic doctrinaire mode, it has removed the issue from the empirical domain. Consider pain. It is generally agreed that pain has survival value. Physicalism considers it to be either physical (e.g. activation of C-fibers in the PNS), or else a causally inert automatic by-product of brain function. Neither alternative is tenable. Far from being an automatic by-product of brain function, pain is an end-point of mechanisms that modulate it. Pain is innate, evoked in the CNS, and therefore mental.

A3.3 The twentieth century. At the beginning of the last century psychology was the science of the mind. But then Physicalistic philosophers argued that because the mind is neither publicly observable, nor does it make a difference to what is observable, Occam's razor requires that the mind be removed from science. As a result, Psychology ceased to be the science of the mind, and became, instead (for a period of time) the science of behavior. The study of subjects such as the emotions came to a virtual halt. The acceptance of the currently held theory of color (Hering's double-opponent theory) was delayed by several decades, because the psychophysical methods used relied on responses to subjective experience. Neuroscientists, too, have shunned the study of the mind as philosophically incorrect.

A3.4 The last decade. During the last decade there was an abrupt change of attitude toward the possibility and desirability of the empirical study of the mind. The fact that Francis Crick made a transition from molecular biology to the study of (visual) consciousness has contributed to the change in mood. However, this mood change has left the entrenched conceptions untouched: Physicalism has remained the dominant doctrine—its dominance reflected by the proposal, in Principles of Neural Science, that Physicalism is the conceptual framework for the study of the mind in the new century (Schwartz 2000).

A4 Cognitive Science—combining Physicalism with the computer model of the brain.

A4.1 The intercellular view of neural function and Long-term potentiation (LTP). During the 1940s there were several proposals to account for neural function in terms of intercellular factors of interconnectivity and interaction (Hebb 1949). These proposals considered intracellular factors as mainly providing metabolic infrastructure for intercellular information processing in terms of action potentials. The intercellular orientation received an initial support from its account of activity-dependent long-term potentiation (LTP). The intercellular account, however, does not elucidate the mechanism involved. Nor does it account for emotion-based LTP. Intracellular factors account for both types of LTP (Abel et al. 1998, Cahill and McGaugh 1998), and elucidate the molecular mechanisms involved.

A4.2 Is the output of a neuron computable from its inputs? Warren McCulloch and Walter Pitts (1943) proposed that two input neurons impinging on an output neuron can realize the AND, OR, and NOT functions, and made an analogy with similar basic digital circuits. The output of a neuron, or basic neural net, is computable from its inputs, assuming that neural input and output is limited to neural impulses, and assuming that intracellular factors do not affect that output. It is now known that both assumptions are empirically false. But at that time, the proposal gave impetus to the computer model of the brain, which erroneously implies that no neural function can be uniquely identified with a brain locus.

A4.3 The computer model of the brain. The basic tenet of Cognitive Science is that the brain is a computer (Smolensky 1994). The same program can be executed on computers with different hardware design. In this sense, the program is hardware-independent. Similarly, the view that the brain functions like a computer implies that the same neural function can be realized in brains with different anatomies. In this sense, neural function is anatomy-independent. Mental states are determined by neural function. If neural function is anatomy-independent, then so are mental states. Thus, the computer model of the brain leads to the conclusion that no mental state has unique neuroanatomic correlates. Cognitive Science is a Physicalistic doctrine. As such it denies that mental states can affect the brain. In conclusion, for Cognitive Science, neither the mind nor the brain matters: The first, because it makes no difference—the last because it can be different.

B. Prior Art

Some Relevant Empirical Work

B1 Molecular biology, color, smell, and pain. The genes and the amino acid sequence of several sensory receptors have been identified (Nathans et al. 1986, Buck and Axel 1991). But in a telling contrast, there is no clear agreement as to the cortical areas where color, or smell, is evoked. The application of molecular biology to the management of pain (Borsook 2000) reflects the same epistemological legacy. Pain is thought to be imported into the CNS from the PNS, and then be the result of a network effect.

B2 Correlation of cortical columns in two visual areas with sensory responses. An area in the anterior inferotemporal cortex was discovered, consisting of some 2,000 columns spaced 0.4 mm apart. The shift in the direct stimulus from one column to the next correlates with a just-noticeable difference (JND) response to basic visual forms (Fujita et al. 1992). In the middle temporal (MT) visual area, also known as V5, are eight types of columns spaced about 0.3 mm apart, where each column in a row represents a 45° shift in direction of perceived movement. Direct electrical stimulation of a column type elicits in the monkey the response correlated with the corresponding external stimulus (Britten et al. 1992, Salzman et al. 1992). Inhibition and impairment of V5 affect response to visual motion stimuli (Newsome and Pare 1988, Beckers and Zeki 1995). These findings point to the correlation of subjective sensation with the function of these cortical columns. However, this conclusion is rejected because it is inconsistent with the computational, or information-processing, interpretation of neural function (Held 1994, Newsome 1997).

B3 Some unresolved empirical issues. Apart from the epistemological issues, there are the following, more specific, unresolved issues. Present-day knowledge does not account for the differences in function among direction-orientation columns in V5; or among columns of basic visual forms in the inferotemporal cortex; or among columns in these two areas. More generally, there is no explanation of the difference in function of columns among different modality-specific areas, such as tonotopic maps in the auditory cortex, and color-specific areas in the visual cortex. This problem extends to mental states such as basic fear, hunger, and thirst. This issue is made more complex by plasticity—the process whereby brain loci change structure and function outside, or beyond, normal development.

B4 The delayed application of molecular biology to the study of neural function. Molecular biology has transformed the study of the evolution and the development of the nervous system, but not the study of neural function. A similar situation occurred in regards to the view that the body consists of cells, introduced Theodor Schwann (1839). The acceptance of that view, except for the nervous system, was immediate (Finger 1994). Now, again, there is acceptance of the principle implicit in molecular biology that the causal locus of intercellular function is intracellular, except for nerve cells. Neural function determines mental states. The delayed application of the general concepts implicit in molecular biology to neural function explains, in part, why molecular biology has been virtually absent from the current efforts to identify the neural correlates of consciousness (NCC).

X. References

Aatinski, J T. Coupled one-step reverse transcription and polymerase chain reaction procedure for cloning large cDNA fragments. *Methods in molecular biology*. B A White (ed.). 1997.

Abel, T, K C Martin, D Bartsch, and E R Kandel. Memory suppressor genes: Inhibitory constraints on the storage of long-term memory. *Science*. 1998. 279: 338-341.

Adelman, L M. Molecular computation of solutions to combinatorial problems. *Science*. 1994. 266: 1021-1024.

Agrawal, S and Q Zhao. Antisense therapeutics. *Current opinion in chemical biology*. 1998. 2: 519-528.

Albright, T. Direction and orientation selectivity of neurons in visual area MT of the macaque. *J of Neurophysiology*. 1984. 52: 1106-1130.

Anderson, W F. Gene therapy. *Nature*. 1998. 395: 25-30.

Basebaum, A J and T M Jessell. The perception of pain. *In Principles of Neural Science*. 4th edition. Edited by E R Kandel et al. New York: McGraw-Hill. 2000.

Beckers, G and S Zeki. The consequences of inactivating areas V1 and V5 on visual perception. *Brain*. 1995. 118: 49-60.

Bethke, B D, and B Sauer. Rapid generation of isogenic mammalian cell line expressing recombinant transgenes by use of Cre Recombinase. *Methods in molecular biology*. E Kmiec (ed.). Totowa, N.J.: Humana Press. 2000.

Borsook, D, (ed.). *Molecular neurobiology of pain*. Seattle, Wash. IASP Press. 1997.

Braun, A R, et al. Dissociated pattern of activity in visual cortices and their projections during human rapid eye movement sleep. *Science*. 1998. 279: 91-95.

Britten, K H, M N Shalden, W T Newsome and J A Movshon. The analysis of visual motion: a comparison of neuronal psychophysical performance. *J neuroscience*. 1992. 4745-4761.

Brodmann, K. *Vergleichende lokalisationslehre der grosshirnhinde*. Leipizig: Barth. 1909.

Buck, L B. Smell and taste: the chemical senses. In *Principles of Neural Science*. 4th edition. Edited by E R Kandel et al. New York: McGraw-Hill. 2000.

Buck, L B. and R Axel. A novel multigene family may encode odorant receptors. *Cell*. 1991. 65: 175-187.

Burcin, M M, et al. Adenovirus-mediated regulable target gene expression in vivo. *PNAS, USA*. 1999. 96: 355-360.

Buxhoevden, D P, et al. Quantitative analysis of cell columns in the cerebral cortex. *J. of neuroscience methods*. 2000. 97: 7-17.

C. Elegans Sequencing Consortium. Genome sequence of the nematode *C. Elegans*: A platform for investigation biology. *Science*. 1998. 282: 2017-18.

Cahill, L, and J McGaugh. Mechanism of emotional arousal and lasting declarative memory. *TINS*. 1998. 21: 294-299.

Celis, J E, et al. Human and mouse proteomic databases: Novel resources in the protein universe. *FEBS. Lett*. 1998. 430: 64-72.

Chalmers, D J. What is a neural correlate of consciousness? In *Neural correlates of consciousness: Empirical and conceptual questions*. Edited by T Metzinger. 2000. Cambridge. Mass. The MIT Press.

Chee, M, R Yang, E Hubbell, A Berno, X C huang, D Stern, J Winkler, D J Lockhart, M S Morris and S P A Fodor. Accessing genetic information with high-density DNA arrays. *Science*. 1996. 274: 610-614.

Cinelli, A R. High-definition mapping of neuronal activity using voltage-sensitive dyes. *Methods*. 2000. 21: 349-372.

Davidson, B. et al. A model system for in vivo gene transfer into the central nervous system using adenoviral vector. *Nature Genetics*. 1993. 3: 219-23.

Dehaene, Stanislas. *The number sense: How the mind creates mathematics*. 1997. Oxford: Oxford University press.

Demeneix, B A., M Ghorbel, and D Goula. Optimizing polyethylenimine-based gene transfer into mammalian brain for analysis of promoter regulation and protein function. *Gene targeting protocols*. E Kmiec (ed.). Totowa, N.J.: Humana Press. Inc. 2000.

Dobelle, W. et al. A prostheses for the deaf based on cortical stimulation. *Ann Otol*. 1973. 82: 445-463.

Dobelle, W. et al. Artificial vision for the blind: Electrical stimulation of the visual cortex offers hope for a functional prostheses. 1974. *Science*. 183: 440-444.

Doering, L C. Components of cell and gene therapy for neurological disorders. *Molecular medicine and gene therapy*. Edited by T F Krestina. 2001. New York: Wiley-Liss Favorov, O. and B L Whitsel. Spatial organization of the peripheral input to area 1 cell columns. I. The detection of "segregates". *Brain res rev*. 1988. 472: 25-42.

Finger, S. *Origins of neuroscience*. Oxford. Oxford University Press. 1994.

Finegold, A A, et al. A paracrine paradigm for in vivo gene therapy in the central nervous system: treatment of chronic pain. *Human gene therapy*. 1999. 10:1251-1257.

Fujita, I, K Tanaka, M Ito and K Cheng. Columns for visual features of objects in monkey inferotemporal cortex. *Nature*. 1992. 360: 343-346.

Garber, K. An end to Alzheimer's? *Technology Review*. March 2001.

Gershorn, E S, J A Bander, et al. Closing in on the genes for manic-depressive illness and schizophrenia. *Neuropharmacology*. 1998. 18: 233-42.

Gilbertson, T A, S Damak and R F Margolskee. The molecular physiology of taste transduction. *Current opinion in neurobiology*. 2000. 10: 519-527.

Hadjikhani, N, A K Liu, A M Dale, P Cavanagh, R B H and Tootell. Retinocopy and color sensitivity in human visual cortical area V8. *Nature neuroscience*. 1998. 3: 235-241.

Hebb, D O. *The organization of behavior*. New York: Wiley. 1949.

Held, R. Perception and its neuronal mechanisms. *Neurobiology of cognition*. P D Eimas and A M. Galoburda (eds.). The MIT Press. 1994.

Hering, E. *Outline of a theory of the light sense*. Trans. by Hurvich and Jameson. Cambridge: Harvard University Press. 1920/1964.

Hermann, T. and D J Patel. Biochemistry-adaptive recognition by nucleic acid aptamers. *Science*. 2000. 287: 820-825.

Jameson, D. and L M Hurvich. Essay concerning color vision. *Annual Review of Psychology*. 1989. 40: 1-32.

Jerne, N K. Antibodies and learning: selection versus instruction. In *The neurosciences: A study program*. Quatron, G, T Melneckuck and F O Schmitt (eds). New York: Rockefeller University Press. 1967.

Kay, B J, Winter, and J McCafferty. *Phage display of peptides and proteins: A laboratory manual* London: Academic Press. 1996.

Kelly, J P. Hearing. In *Principles of neural science*. 3rd edition. Edited by E R Kandel et al. New York: Elsevier Science Publishing. 1991.

Klose, J. Fractionated extraction of total tissue protein from mouse and human for 2-D electrophoresis. *Methods Mol. Biol*. 1999. 112: 147-172.

Klose, J. Large-gel 2D electrophoresis. 1999. *Methods of Mol. Biol*. 112: 147-172.

Kmiec, E B. Gene therapy. *Am. Scientist*. 1999. 87: 240-47.

Kohl, S et al. Total colorblindness is caused by mutations in the gene encoding for the a-subunit of the cone photoreceptor cGMP-gated cation channel. *Nature genetics*. 1998. 19: 257-259.

Link, A J, et al. Direct analysis of protein complexes using mass spectroscopy. *Nature Biotechnol*. 1999. 17: 676-682.

Locke, John. *An essay concerning human understanding*. Edited with an introduction by P H Niddith. Oxford: Clarendon Press. 1705/1975.

MacBeath and S L Schreiber. Printing proteins as microarrays for high-throughput function determination. *Science*. 2000. 289: 1760-1763.

Maulik, S, and S Patel. *Molecular biotechnology*. New York: Wily-Liss. 1997.

Martin, J H. Coding and processing of sensory information. In *Principles of neural science*. 3rd ed. Edited by E R Kandel et al. New York: Elsevier. 1991.

McCulloch, W S and W H Pitts. A Logical calculus of the ideas immanent in nervous activity. In *Embodiments of mind*. W. S. McCulloch. The MIT Press. 1943/1970.

Melzak, R. Phantom limbs and the concept of the neuromatrix. *TINS*. 1990, 13: 88-92.

Miyamoto, R T, M J Osberger, A M Robbins, W A Nyers, & Kessler. Prelingually deafened children's performance with the nucleus multi-channel cochlear implant *The American Journal of Otology*. 1993. 14: 437-445.

Mountcastle, V B. The columnar organization of the neocortex. *Brain*. 1997: 120: 701-22.

Nabel, G J. Development of optimized vectors for gene therapy. *PNAS USA*. 1999. 96: 324-326.

Nathans, J, T D Hogness, D S. Molecular genetics of human color vision: the genes encoding blue green and red pigments. *Science*. 1986. 232:193-202.

Newsome, W T. Perceptual processes. In *Conversations in the Cognitive Neurosciences*. Edited by M S Gazzaniga. Cambridge. Mass. The MIT Pres. 1997.

Newsome, W T, and E B Pare. A selective impairment of motion perception following lesions of the middle temporal visual area (MT). *J. Neuroscience*. 1988. 8: 2201-2211.

O'Leary, D D M, et al. Molecular development of sensory maps: Representing sights and smells in the brain. *Cell*. 1999. 96: 255-269.

Paulus, W, et al. Differential inhibition of chromatic and achromatic perception by transcranial magnetic stimulation of the human visual cortex. *NeuroReport*. 1999. 10: 1245-1248.

Penfield, W, and T Rassmussen. *The cerebral cortex of man: A clinical study of localization of function*. New York: Macmillan. 1950.

Pennington, S R, and M J Dunn, Editors. *Proteomics: From protein sequence to function*. 2001. New York: Springer-Verlag.

Recanzone, G, C Schneider and M Merzenich. Plasticity in the frequency representation of primary auditory cortex following discrimination training in adult owl monkeys. *J. of neuroscience*. 1993. 12: 87-103.

Rosenbleuth, A, N Wiener, and J Bieglow. Behavior, purpose, and teleology. *Philosophy of science*. January 1943. 18-19.

Sakurai. T, et al. Orexins and orexins receptors: a family of hypothalamic neuropeptides and G protein-coupled receptors that regulate feeding behavior. *Cell*. 1998. 92: 573-85.

Salzman, C D, C M Murasugi, K H Britten, W T Newsome. Microstimulation of visual area MT: effects on direction discrimination performance. *J neuroscience*. 1992. 12: 2478-2492.

Schwartz, J H. Consciousnesses and the neurobiology of twenty-first century. In *Principles of Neural Science*. 4th edition. E R Kandel et al. New York: McGraw-Hill. 2000.

Sehgal, A, et al. Rhythmic expression of timeless: A basis for promoting circadian cycles in period gene autoregulation. *Science*. 1995. 270: 808-810.

Seidman, J G. Screening of recombinant DNA libraries. *Current protocols in molecular biology*. New York: John Wiley and Sons, Inc. 2000.

Smolensky, P. Computational models of minds. *A companion to the philosophy of mind*. Guttenplan (ed.). Oxford: Blackwell Publishers, Ltd. 1994.

Sokoloff, L. *Metabolic probes of central nervous system in experimental animals and man*. Sauderland, Mass.: Sinauer. 1984.

Sperry, R. Neurology and the mind-body problem. *American scientist*. 1952. 40: 291-312.

Stapp, H P. *Mind and quantum mechanics*. Springer verlag. 1993.

Stevensm S S. *Psychophysics*. New Brunswick: Transaction Books. 1975/1986.

Todd, P K and K J Mack. Sensory stimulation increases cortical expression of the Fragile X Mental Retardation Protein in vivo. *Molecular Brain Research*. 2000. 80: 17-25.

Tootel, R B H, et al. Visual motion aftereffect in cortical area MT as revealed by fMRI. *Nature*. 1995, 575: 139-141.

Waltzman, S B, N I Cohen & W H Shapiro. Use of multichannel cochlear implant in the congenitally and prelingually deaf population. *Laryngoscope*. 1992, 102: 395-399.

Wilson, S P, et al. Antihyperalgesic effects of infection with preproenkephalin-encoding herpesvirus. *PNAS, USA*. 1999. 96: 3211-3216.

The Conceptual Framework

C. An overview

C1 Molecular psychophysics. The contribution of molecular biology to the study of the mind has been indirect. At present there is no discipline of science that systematically correlates simple sensations and other elementary mental states with molecular constitution of activated brain loci. The conceptual framework combines the fact that elementary mental states are innate with a principle implicit in molecular biology that the causal locus of intercellular function is intracellular, thus defining a new discipline, which may be called molecular psychophysics.

C2 Some basic notions. The three basic notions of the conceptual framework that are directly relevant to the present subject are introduced below. Other aspects are briefly reviewed in Appendix A.

C2.1 The senses and sensations. The information the brain receives from sensory receptors is devoid of sensory qualities. Sensory qualities are innate, evoked in the brain, and are thus mental. Sweetness, for example, is not a property of sugar, nor does sweet taste originate in taste receptors. Instead, that sensation is innate, and is evoked in the brain. The same applies to the middle C pitch, the color red, or the sensation of pain.

C2.2 Elementary mental states—an initial characterization. A tune is a one-dimensional pattern of pitch elements, and an image is a two-dimensional pattern of picture elements. Any pitch, by itself, is devoid of pattern, and does not have any smaller constituents—it is an elementary mental state. This, and all other elementary mental states have the attributes of intensity and duration.

C2.3 The causal locus of intercellular function is intracellular. Molecular biology has demonstrated that the causal locus of cellular function is intracellular. This intracellular causal locus applies to nerve cells as to any other cell type. The structure and function of a neuron is primarily determined by its constitutively expressed cell-specific proteins (CELS).

C3 The neural correlates of elementary mental states. Neural function determines mental states. Localized neural function is the primary determinant of elementary mental states. The CELS that determine local neural function also determine the qualitative nature of the evoked elementary mental state.

C4 Correlation criterion. CELS are the correlate of a given elementary mental state if their inactivation selectively impairs or abolishes the otherwise normal behavioral response to the external stimulus that elicits that mental state. Thus, CELS in the gustatory cortex are the correlates of sweet taste if their inactivation impairs or abolishes the behavioral response to sugar, but not the behavioral responses to substances normally taken to be salty, sour, or bitter.

C5 The construction of a database of the neural correlates of elementary mental states. The systematic identification of CELS protein correlates of elementary mental states would culminate in a database of such correlates, which is a subset of all CELS proteins in the brain.

D. Elementary Mental States

D1 Elementary mental states have no smaller internal constituents.

D1.1 Taste. Elementary mental states are innate, evoked in the brain, and other than intensity and duration, have no internal constituents. The taste sensations of sweet, salty, sour, and bitter are innate. Their innateness is reflected by the fact that infants, without any prior experience, like sweet and dislike bitter.

D1.2 Taste and affect. Innate taste preferences are separate components from the taste itself, and are often subject to age, sex, and cultural differences. The affective component of sweet taste, for example, can be blocked by endorphin receptors antagonists, such as naloxone, in the nucleus accumbens.

D1.3 The spatial component in vision touch and pain. The spatial component of simple sensation, such as a light touch or a painful stimulus, on the surface of the body is a separate component from the sensory element itself. Similarly, a simple visual stimulus is separable from its location in the visual field.

D2 Exteroreceptors and interoreceptors. Exteroreceptors such as the eyes and ears provide information about the world outside. In primates, the last stages of processing exteroreceptor information involving vision, hearing, touch, taste, and smell, take place in modality-specific areas of the cerebral cortex. Interoreceptors provide information about the conditions within the body such as the water and glucose levels in the blood, which typically give rise to sensations of hunger and thirst respectively. The cerebral cortex also provides top-down regulation for interoreceptor-related elementary mental states such as hunger, thirst, fear, or pleasure. But the loci specific to them are subcortical. Consider hunger, in contrast to taste. It provides information about the glucose level in the blood—which is an internal state of the body. Hunger does not have a modality-specific area in the cerebral cortex. The same applies to thirst and to basic emotions, such as innate fear. In order to simplify the presentation, the focus will be on sensations that are represented by modality-specific cortical areas.

D3 Three levels of organization. Red, green, yellow, and blue are sensory elements in the submodality of color, in the sensory modality of vision. This reflects three levels of organization, where each basic color is the first level; the submodality is the second level; and the sensory modality is the third level of unimodal organization. The focus of this presentation is on sensory elements and submodalities, rather than on sensory modalities and perception. The table below illustrates the three levels or organization for basic colors and tastes.

| Organization level | Examples | |
| --- | --- | --- |
| * Modality: | Vision | Taste |
| * Submodality: | Color | Basic taste |
| * Elements: | White/black red/green blue/yellow | Sweet, salty, sour, bitter, and umami. |

D4 Elementary mental states contrasted with unimodal perception. A picture involves a spatial pattern of visual elements. A tune consists of a temporal pattern of elements of pitch. The integration of submodalities within a sensory modality is a unimodal percept. Imagine seeing a red ball thrown toward you. That unimodal percept integrates submodalities related to the redness and roundness of the ball with those relating to depth and movement. This presentation does not directly address this third level of organization, and focuses instead on sensory elements and their submodalities. Sensory elements, for example, typically are devoid of pattern information. Elementary mental states are innate, evoked in the CNS and, other than intensity and duration, have no more basic constituents.

D5 An experimental proof that sensations are innate and evoked in the CNS.

D5.1 Afferent neurons convey information devoid of sensory quality. Neurons convey to the brain information from the different sensory receptors by means of frequency modulation of action potentials. The propagation velocity of an action potential is substantially fixed for a given neuron, and the strength of the impulses is also substantially constant. Such frequency modulation can transmit information, but not sensation. Consequently, the qualitative nature of sensory information is determined by its brain targets (Sperry 1952). This explains the fact that persons born without a limb typically experience pain and other sensations in the absent limb (Melzak 1991). By way of analogy, consider the Internet. Information received over the Internet that is directed to the speakers produces sound, and information directed to the visual display produces color and light. Yet, there is nothing qualitatively sound-like, or color-like, about received bit-patterns. It is the target device that determines the qualitative nature, or the sensory modality, of the output.

D5.2 Intrinsic local properties. If a particular sensation is not received from the PNS, then it could be elicited by the direct (electrical, magnetic, or chemical) stimulus of a modality-specific cortical area. A direct stimulus contrasts with input from the senses in being devoid of pattern information typically received from external stimuli. The direct stimulus is also devoid of the normal transformation of the input prior to reaching the modality-specific cortical area: It is information-poor. Moreover, the same type of stimulus that evokes the sensation of sound in the auditory cortex would evoke the sensation of touch in the somatosensory cortex. The direct stimulus does not contribute to the qualitative nature of the response. In conclusion, the evoked neural function is an intrinsic property of stimulated loci.

D5.3 Stimulating the auditory nerve of children born non-cortically deaf produces sound. Consider sound. It the sensation of sound is received from the ears, then the direct stimulation that bypasses the sensory receptors in children born non-cortically could not, and would not, evoke sensations of sound. Yet, it does. Such stimulation does not require the presence of air vibration, and bypasses the auditory receptors. This fact demonstrates that sound is neither a physical property of air vibration, nor a sensation originating in the ears. This fact underlies the successful use of cochlear implants in children born non-cortically deaf (Waltzman et al. 1992, Miyamoto et al. 1993). It also constitutes a conclusive disconfirmation of the tabula rasa assumption, and its Physicalistic variant.

D5.4 Cortical prostheses. William Dobelle proposed auditory (1973) and visual (1974) prostheses, that bypass the auditory nerve and optic nerve respectively. Such prostheses have been developed, demonstrating that the sensation of sound, color, and light are evoked in the CNS, and not received from the PNS.

E. Submodality-Specific Areas of the Cerebral Cortex

E1 Modality-specific areas of the cerebral cortex. Each sensory modality is processed in a separate, spatially contiguous cortical area. For example, modality-specific thalamic nuclei for olfaction project their primary output to the orbitofrontal cortex, making that cortical area modality-specific for olfaction. The initial target for the thalamic projection is the primary modality-specific cortical area. The modality-specific information from the thalamus relates to different submodalities. Each submodality is then processed in distinct secondary areas within each modality-specific cortical area. The output of this unimodal information is then projected to association areas, which are not modality-specific.

E2 Primary and secondary areas in the somatosensory cortex. Conventionally, Brodmann areas (BAs) 3a, 3b, 1, and 2 are collectively called the primary somatosensory cortex. Primary sensory cortex is one that receives its primary input from the corresponding modality-specific thalamic nuclei. By this criterion BA3a and BA3b are primary sensory cortical area, while BA1 and BA2 are secondary sensory cortical areas. More precisely, BA1 receives its main input from BA3b, and is submodality-specific for light touch (input from rapidly adapting mechanoreceptors). BA2 integrates input from BA3b about pressure (from slowly adapting mechanoreceptors with information about light touch from BA1.

E3 Columns in submodality-specific cortical areas. The column is a unit of elementary function in the cerebral cortex. The column also has been identified as a unit of subjective sensation in several submodality-specific cortical areas. In the visual cortex, these areas include columns in V5 for the sensation of direction of movement, columns in the anterior inferotemporal cortex for basic visual forms. In the somatosensory cortex, the direct electrical stimulation of BA1 in normal awake human subjects produce the sensation of light touch in the corresponding part of the body surface (Penfield 1950). Mountcastle (1957) demonstrated its columnar organization of the somatosensory cortex. Favorov and Whitsel (1988) demonstrated the correlation of direct stimulation of columns in BA1 with behavioral responses.

E4 Spatial contiguity. The cortical column is a spatially contiguous cluster of neurons. A submodality-specific cortical area is a spatially contiguous area within a modality-specific area. A modality-specific area is a spatially contiguous area in the cortical sheet.

F. Correlating Different Levels of Response to an External Stimulus

F1 Four levels of response to an external stimulus. Consider different aspects of the response of an awake, normal human subject to an external stimulus, such as air vibration produced by striking the middle C key in a piano:
1. The person may exhibit a behavioral response, such as point to the piano key.
2. Some brain loci, including the auditory cortex, would be transiently activated.
3. Some auditory cortex neurons would manifest inter- and intracellular activation
4. The person would experience the auditory sensation of the middle C pitch.

Psychophysics provides methods to correlate the externally observable behavioral response with simple subjective sensations. Neuroscience provides methods to correlate that behavioral response with transient activation of some brain loci. Molecular psychophysics provides the conceptual framework for correlating the behavioral response with molecular constituents of the activated brain loci.

F2 Correlating behavioral response to stimuli with subjective states.

F2.1 The observable correlates of unobservable subjective states. Given a stimulus, such as taste of sugar or salt, for example, the normal, awake person would experience the sensation of sweetness or saltiness, respectively. These taste sensations subjective states: They are not observable by others. This intrinsic non-observability by others is the defining characteristic of the mental. The same stimuli that elicit the subjective states can also elicit behavioral response that is observable. Correlating subjective states with behavioral responses makes them indirectly observable.

F2.2 The response to just noticeable difference. Consider the sensation of sound. Like all elementary mental states, the sensation of sound has the dimension of intensity and duration. Assume that a scientist with normal hearing acts as the subject to a psychophysical experiment with sound. Keeping the amplitude, or loudness constant, the frequency of air vibration is gradually increased from one cycle per second up, the scientist will be able to discriminate some 3,075 distinct sounds in the range of 20-20,000 Hz (Stevens 1975/1986). Unlike the gradual change in frequency, the change in subjective experience consists of a step-function. Such a discrete transition is called just noticeable difference (JND). In the case of sound, the JND is called pitch. As the term indicates, JND is the smallest increment of subjective experience. Since it is not publicly observable, the behavioral response to it is a fundamental unit of psychophysics. The mapping produced by the scientist as a subject is then the basis for testing the JND responses of others.

F3 Correlating behavioral responses with preferentially activated brain loci.

F3.1 External, and direct, stimulation of columns in BA1. In response to external stimuli, some brain loci would be preferentially activated in addition to the subjective states and the behavioral response. Such activation involves increased metabolism of glucose and oxygen, and increased evoked potential activity. Consider the sensation of light touch. An external stimulus of light touch on any part on the surface of the body produces preferential activation of columns in BA 1. Conversely, the direct electrical (or other) stimulus of any column in BA1 in an awake, normal person, elicits the sensation of light touch in the corresponding part of the body surface.

F3.2 The deactivation of columns in BA1 selectively abolish behavioral response. The inactivation of any part of BA1 causes a loss of sensation of light touch in the corresponding part of the body surface, without affecting the response to other submodalities of the somatosensory cortex. For example, the deactivation of BA2 does not affect the sensation of light touch.

F4 Brain loci related to the three levels of organization. The initial two variables that need to be correlated are behavioral response R (the JND response), and the brain locus preferentially activated by the external stimulus, L. These two variables can be addressed at each of the three levels of organization as follows:

| | Sensory modality | Submodality | Submodality element |
|---|---|---|---|
| Behavioral response | R" | R' | R |
| Brain loci | L" | L' | L |

F4.1 Partial interdependence of submodality elements. Columns within a submodality-specific cortical area are interconnected. For each column in V5, for example, there is a column in an adjacent row representing the opposite direction (Albright 1995). The interconnection and interaction between such opposing columns is manifested by opposite after-image (Tootel et al 1995). Such interconnection and interaction does not obliterate the preferential columnar activation in response to an external or to a direct stimulus. Similarly, the effect of inactivating a submodality-specific cortical column would selectively impair or abolish the corresponding behavioral response.

F4.2 Relative independence of submodality-specific areas in the visual cortex. A person can be blind without being deaf, or be deaf without being blind, because sensory modalities are relatively independent. The same applies to submodalities. Some persons who suffer lesions due to stroke in V5 become blind to movement. This effect can be reversibly induced by inhibiting the function of V5 by means such as transcranial magnetic stimulation (TMS) (Becker and Zeki 1995). Such submodality-related dysfunction leaves other submodalities of vision, such as form and color, unaffected. Similarly, some persons become color-blind due to lesions in the visual cortex (central achromatopsia), leave intact other aspects of vision. More generally, inactivating (the terms inactivation and deactivation are used inter-changeably) brain loci L' impairs or abolishes behavioral response R'.

F4.3 Submodality-specific areas with a single submodality element. The same sensation of light touch may be evoked by stimulating different points on the body surface. BA1, which maps the body for the sensation of light touch, is, therefore, a submodality-specific area with a single sensory element.

F5 Symbolic formulation. For each of the three levels of organization, the relation between the inactivation of a brain locus, and the consequent abolition of behavioral response is stated below, where $L\downarrow$ designates inactivation, and $R\downarrow$ designates abolished behavioral response in the presence of an external stimulus.

| | Submodality element (e.g. red) L | Submodality (e.g. color) L' | Sensory modality (e.g. vision) L" |
|---|---|---|---|
| Inactivation | $L\downarrow \supset R\downarrow$ | $L'\downarrow \supset R'\downarrow$ | $L"\downarrow \supset R"\downarrow$ |

F6 A criterion for identifying L in terms of the selective effects of its deactivation. Any neural function that can be selectively abolished by the deactivation of a brain locus is localizable. Similarly, the neural correlate of an elementary mental state is localizable if it can be selectively abolished by the deactivation of a brain locus. If j and k are different sensory elements of the same submodality, then JND response correlates with differential columnar activation in the secondary modality-specific area that mediates the behavioral response. Thus, the inactivation brain locus Lj abolishes behavioral response Rj, but not behavioral response Rk. The following illustrates how the identification criterion is involved in determining whether a brain locus is, or is not, related to the elementary mental states of innate fear and pain.

F7 Applying the identification criterion to fear and pain.

F7.1 Is the neural correlate of fear localizable? Elementary mental states, such as hunger and thirst, which relate to interoreceptors and subcortical loci, are subject to top-down cortical control. This fact is commonly taken to imply either that the cortex is necessary for these mental states, or that these mental states are not localizable. The correlation criterion provides a method of addressing this issue.

F7.2 Pain. The application of a painful stimulus to the surface of the body causes activation of several brain loci, including the somatosensory cortex. However, the direct stimulation of the somatosensory cortex does not elicit pain response, and its deactivation does not abolish the pain response. For this reason pain is not a submodality of the somatosensory cortex. Pain, like any innate capability, has molecular correlates. Their deactivation would selectively abolish the pain response. The same reasoning applies to other elementary mental states, such as hunger and thirst, and their relation to subcortical loci (hypothalamic nuclei).

G. The Causal Locus of Neural Function is Intracellular and Structure-Dependent G1 Intracellular factors affect the output of the neuron. The computer model severs the function of the brain and its mental states from the anatomy of the brain. It is based on the assumption that intracellular factors do not affect the output of neurons. This assumption is empirically false. The output of different types of photoreceptors to the same photon input is determined by cell-type specific opsin protein. Moreover, intracellular factors produce a variable output. Consider the typical, basic sleep cycle of 24 hours and 12 minutes. It is produced by neurons in the suprachiasmatic nucleus of the anterior hypothalamus. But while that cycle is affected by melatonin and other intercellular signal molecules, the basic output of these neurons is produced by intracellular mechanisms, which involves proteins such as Timeless and Period (Sehgal, et al. 1995). Some may consider the function of these neurons to be computational. In that event, it ought to be noted that the computer model of the brain is inconsistent with such intracellular, structure-dependent computation.

G2 A cell is affected by proximate, but not distal, causes. In the causal chain of events affecting a cell, the last, or proximate, cause is necessary, and the non-proximate, or distal causes, are contingent. Different non-proximate events can bring about the same proximate effect. Action potentials in presynaptic neurons, for example, are non-proximate events, and thus contingent. In their absence, the binding of neurotransmitters to the postsynaptic neuron would produce the same effect. Moreover, the same neurotransmitter produces different effects in different receptor subtypes. For this reason, neurotransmitters are distal causes.

G3 The structure of molecules determines their function. Key cellular events occur in the range of 3-4 Å (Lowensten 1999). The study of the three-dimensional structure of molecules in that scale is the basis of supramolecular chemistry and structural biology. The amino acid sequence of a protein, or its primary structure, typically determines its three-dimensional (average) structure, which in turn, is the primary determinant of its function. The binding of two complementary strands of DNA exemplifies the fact that a unique structure often confers on a molecule a unique function. This tight coupling of structure and function is also reflected by evolutionary convergence to the same twenty amino acids, the near universal nucleic acid code for these amino acids, and the unique function of metaloproteins. Neurons are cells. Therefore, neural function is structure-dependent and can be, and often is, unique.

H. Cell Differentiation and Protein Specificity

H1 Cell differentiation. During the development of a multicellular organism, successive stages of selective gene expression transform an embryonic stem cell into a mature differentiated cell. Each stage of selective gene expression results in a corresponding change in the protein specificity of the cell. It is this specificity that accounts for the differences in both the structure and the function of skin, muscle, and bone and nerve cells. Organs of the body, such as bones, muscles, and skin, are spatially contiguous. During the course of life, the size and shape of these organs change, but their contiguity and topology remain unchanged. The observed spatial contiguity is a manifestation of tissue-specific and cell-specific protein commonalities.

H2 Logical tree of cell fate. Cell-fate lineage may be viewed in terms of its location on a logical tree, with the embryonic stem cell as the trunk, and each cell-type occupying an end-point branch. The branching sequence producing any end-point position is unique.

H3 Viewing the logic tree from an end-point branch. A cell type has protein types that set it apart from other cell types. Subtypes of that cell type have, in addition, protein types that set each apart from the other cell subtypes. If P designates protein specific to a given cell type, P' designates proteins common to subtype of the cell type, and P0 designates all other protein types, then the protein specificity Q of a cell subtype is Q=P+P'+P0. Smell receptors and photoreceptors, for example, are each characterized by a unique protein.

H4 Information implicit in any end-point branch of the logic tree. Any end point determines:
1. The cell type
2. Cell fate lineage
3. The proteins specific to that cell type
4. The cell's phenotype
5. The function of that cell type
6. The location of that cell type in the organism.

H5 Constitutively expressed cell-specific proteins of photoreceptors in humans. Humans have three types of wavelength-specific cone receptors, and one type of rod receptors, which is not wavelength-specific. Each photoreceptor type is characterized by a unique opsin protein; the cone receptors have some proteins in common; and the entire photoreceptor class has a number of proteins in common. The unique protein of each photoreceptor type, protein common to cone photoreceptors, and those common with rod receptors as well may be characterized as follows:

| P | P' | P" |
|---|----|----|
| Opsin proteins unique to each receptor | Proteins common to cone photoreceptors | Proteins common to all photoreceptors |

H6 Temporal branching and hierarchical spatial contiguity.

H6.1 Temporal branching and nesting of contiguous areas. The temporal sequence of differentiation stages typically results in a spatial outside-in direction. Differentiation of cortical areas begins in the third trimester with signals from the thalamus, then by local signals, and finally fine-tuned by input from sensory receptors via the thalamus. Modality-specific cortical areas specialize first, submodality-specific areas specialize next, and cortical columns in submodality-specific areas specialize last. This results in the nesting of contiguous expression zones. As for example, V5 is a spatially contiguous area within the visual cortex. The visual cortex differentiates first; visual area V5 subsequently; and columns in V5 differentiate last.

6.3 Hierarchical spatial contiguity of in the nervous system. PNS ganglia and CNS nuclei exemplify spatial contiguity in the nervous system. This contiguity is hierarchical. In sensory areas in the cerebral cortex, for example, the column is a cluster of contiguous neurons, in a spatially contiguous submodality-specific area, within a spatially contiguous modality-specific area. These spatial contiguities are phenotypical manifestations of gene expression zones.

H7 Plasticity is mediated by gene expression. The response of the cell to internal and external cues consists of selections from the finite and discrete genome's menu (Jerne 1967). The conceptual framework extends Jerne's insight to plasticity. Persistent stimuli induce plasticity (Recanzone et al. 1993). The plasticity response is maximal during the postnatal critical period (Wiesel and Hubel 1965). This period is about two years in humans and about a month in the mice. Therefore persistent stimuli during the postnatal critical period selectively amplify the mRNA transcription of the correlated behavioral response.

J. The Relation of Cels Proteins P, Brain Loci L, and Behavioral Responses R

J1 Rank-ordered dependent function and dysfunction of CELS proteins. The function of CELS protein P is necessary for the function of brain locus L; the function of brain locus L is necessary for behavioral response R. Therefore, the function of P is necessary for behavioral response R. Hence, the inactivation of P abolishes the function of brain locus L; the inactivation of L abolishes behavioral response R. For this reason, the inactivation of P abolishes behavioral response R. Thus R, the JND response to external stimulus, signifies the preferential activation of brain locus L, and its L-specific proteins P. This relation also applies to the second level of organization, between submodality-specific cortical areas L', behavioral responses R', and CELS proteins P'.

J2 Rank-ordered dysfunction of photoreceptors. The function, or dysfunction, of CELS proteins is rank-dependent. Consider photoreceptors again. A dysfunction in the opsin protein for a long-wave cone photoreceptor causes the behavioral response of red-blindness, but it leaves unaffected the behavioral response to the medium- and short-wavelength cone photoreceptors (Nathans et al. 1986). A dysfunction of protein common to cone receptors causes the behavioral response of achromatopsia, or total colorblindness (Kohl et al. 1998), but leaves unaffected black and white rod vision. A dysfunction of a protein common to all photoreceptor types (including rods) affects general vision, causing several types of Retinitis Pigmentosa (Maulik and Patel 1997). The rank-dependent dysfunction is symbolically represented as follows:

| Submodality element $P\downarrow \supset R\downarrow$ | Submodality $P'\downarrow \supset R'\downarrow$ | Sensory modality $P''\downarrow \supset R''\downarrow$ |
|---|---|---|
| Long wave opsin protein Colorblindness to red | Cone-specific protein Achromatopsia | Photoreceptor-specific Retinitis Pigmentosa |

J4 Cell-specific proteins and housekeeping proteins. Housekeeping proteins are present in virtually all cell types. The ubiquity of their function makes them critical for survival. There exists some redundancy in their function, which provides something of a fail-soft capability. In contrast, cell-specific proteins, as those characterizing photoreceptors and smell receptors are unique. Their dysfunction abolishes the related neural function. In these sensory receptors, proteins of the next level of organization act in concert. The convention distinction between monogenic and polygenic is inadequate for cell-specific proteins. A dysfunction in any of these proteins would impair or abolish the related neural function.

J5 Situations where a submodality class has a single member. In cases where a submodality, such as light touch, or the visual sensation of a point of light in the visual field under scotopic conditions, then the submodality class has just a single member, and P'=P.

J6 Definition of P by selective inactivation. If Pj is a CELS protein of Lj, and Pk is a CELS protein of locus Lk, then the inactivation of Pj would impair or abolish behavioral response Rj, but not Rk response. The locus of P also defines L. Hence, the selective abolition of behavioral response R by the deactivation of P confirms locus L.

K. Constitutively Expressed Cell-Specific, and Locus-Specific, Proteins in the Brain K1 The K1 database. The identification and compilation of CNS CELS proteins that correlate with elementary mental states would constitute the K1 database. Such a database is a subset of the constitutively expressed cell-specific proteins in the brain.

K2 The K2 database. The identification and compilation of cell-types in terms of their cell-fate lineage would constitute the K2 database of the constitutively expressed cell-specific proteins in the brain. The K2 database is a subset the constitutively expressed cell-specific proteins in the body.

L. A Numbering System for Cell Types and for Elementary Mental States

L1 Characterizing cell types in terms of their location in a logical tree. The end-point position of any cell-type on a cell-fate lineage tree is unique. This cell-fate tree is best viewed in terms of the number of differentiation stages necessary to transform an embryonic stem cell into any mature cell type in vitro. It may be represented by a number of digits, which can be made binary (for cases where the number of outcomes at a choice point is greater then two), reflecting the number of choice points. The mature *C. Elegans*, for example, has 959 cells, 350 of which are neurons. A sixteen-bit number would characterize every cell type. A germ cell is the result of five branching stages (zygote→P1→P2→P3→P4→germ cell); therefore the five high-order bits of the sixteen-bit number characterize it. However, the detailed cell-fate lineage for mammals is not known.

L2 Assigning provisional numbers to locus-specific cell types.

L2.1 Phenotype as manifestation of intracellular factors. Cell types and their cell-specific proteins can be mapped, and numbered, before the detail lineage is discovered, and before the proteins themselves are identified. Organs, tissues, and locus-specific cell types are phenotypic manifestations of the constitutively expressed cell-specific proteins. Mapping and numbering the hierarchical organization of locus-specific cells amount to mapping and numbering the correlated cell-specific proteins.

L2.2 Provisional high-order numbers for known brain structures. For this reason, a provisional high-order number would be assigned on the basis of the following considerations. Known brain anatomy is a phenotypic manifestation of gene expression zones. Therefore brain nuclei would each be assigned a provisional two-digit decimal number. Each known subnucleus within a given nucleus would be given a lower-order two-digit decimal number. Similarly, in the cerebral cortex, cytoarchitecture is a phenotypic manifestation of gene expression zones. Thus, in the cortex, a numbering system similar to Brodmann area numbers would be used as provisional two-digit decimal number.

L2.3 The low-order positions uniquely characterize a cell type. The cell-fate lineage tree can be viewed not as diverging from the common trunk, but also as converging from the end-branches to the main branches. This obviates the problem of not knowing lineage of cell-fates in detail, since it is the last differentiation stages the uniquely determine cell-fate. For example, a locus-specific cell in a cortical column of a submodality-specific area would thus have a number reflecting that locus.

L3 The cell-type number characterizes its cell-specific proteins. A locus-specific cell type is a phenotypic manifestation of its protein specificity and function. For this reason, the number system for the position of a cell-type on the cell-fate lineage tree is also a number system for these attributes, including cell-specific proteins and location in the organism or brain.

L4 Numerical representation of CELS proteins.

L4.1 Superscripts to indicate rank-order of locus-specific proteins. For the three levels of organization, the rank-order of CELS proteins have been designated P, P', and P''', respectively. In the systematic mapping of cell-specific, and locus-specific, proteins numerical superscripts are used: P1, P2, P3, ... Pn. P0 designates "all other protein types," which include housekeeping proteins, excreted proteins, and proteins expressed only during development or transiently.

L4.2 Representing the protein specificity of a cell type. In Section H3, the protein specificity of a cell was stated as Q=P+P'+P0, in order to simplify the presentation. With numerical superscripts the same formula is Q=P1+P2+P0. Consider the protein specificity of cone photoreceptors:

Ql=P3+P2+Pl+P0 Long wave cone receptors

Qm=P3+P2+Pm+P0 Medium wave cone receptors

Qs=P3+P2+Ps+P0 Short wave cone receptors

Qn=P3+P2+Pn+P0 Protein specificity n of any cone photoreceptor

Where,

---

P0  All other protein types that are also found elsewhere in the organism
P1  Proteins unique to a cone photoreceptor type (opsins)
P2  Proteins common to cone photoreceptors
P3  Proteins common to all photoreceptors (including rods)

---

L5 A numbering system for elementary mental states.

L5.1 Numbering submodality elements. The three levels of organization sensory elements form a natural basis for a three-part number system. The prefix Q identifies a number as representing an elementary mental state. The high order part represents the sensory modality. Thus, vision, hearing, touch, taste, and smell would be represented by Q1, Q2, Q3, Q4, and Q5 respectively. The second part of the number designates a submodality within a given sensory modality. The low order position represents the sensory element within a given submodality. Here is an example for numbering the basic colors and tastes.

| Modality | Submodality | Submodality elements | | | | | |
|---|---|---|---|---|---|---|---|
| Vision | Basic color | White | Black | Red | Green | Blue | Yellow |
| Q1 | Q1.8 | Q1.8.1 | Q1.8.2 | Q1.8.3 | Q1.8.4 | Q1.8.5 | Q1.8.6 |
| Taste | Basic taste | Sweet | Salty | Sour | Bitter | Umami | |
| Q4 | Q4.1 | Q4.1.1 | Q4.1.2 | Q4.1.3 | Q4.1.4 | Q4.1.5 | |

The modality of sound is Q2. The number of distinct pitch sounds a person with normal hearing can experience is about 3,075. If pitch were submodality Q2.1, then the discrete pitch would be designated Q2.1.1, Q2.1.2, Q2.1.3, ... Q2.1.3075.

L5.2 Numbering elementary mental states that are related to subcortical areas. Elementary mental states that do not have submodality-specific cortical areas, such as thirst or basic emotions, have one or two levels of organization. They would be represented by zero in the high-order part of the three-part number.

L5.3 General, non-specific consciousness. Background consciousness is a single element within one level of organization. Its number therefore is Q0.0.1.

L6 The relation of L4 and L5 numbers. The number assigned an elementary mental state would map into the independently assigned number to the brain locus directly correlated with it. For example, the number assigned to the elementary subjective sensation of light touch would map into the number assigned to the cortical area BA1.

Description of the Invention

M. Summary, Objects and Advantages

M1 A conceptual discovery. The qualitative nature of an elementary mental state is primarily determined by the constitutively expressed locus-specific proteins of brain locus evoking it (K1 proteins).

M2 Methods. The invention provides methods for identifying brain loci, and of constitutively expressed proteins specific to said brain loci, the deactivation of either said loci, or said proteins, selectively impairs the otherwise normal behavioral response to said stimuli.

M3 Advantages. Identified said brain loci and said proteins provide the most selective targets for modulating the correlated elementary mental states, thus increasing the effectiveness, and decreasing the side-effects, of medical intervention.

O. Overview of the Identification Method

O1 An outline of the identification method. Behavioral responses to stimuli are correlated first with subjective states, then with preferentially activated brain loci, and finally with constitutively expressed proteins specific to these brain loci, as follows:

O1.1 Correlating behavioral responses with subjective states. Behavioral responses are correlated with JNDs within the same sensory submodality, to stimuli of constant intensity and duration.

O1.2 Correlating behavioral responses with brain loci. Part I. Preferentially activated brain loci are identified in the mouse using 2D-G, in the monkey using voltage sensitive dyes, and in humans using non-invasive brain imaging.

O1.3 Correlating behavioral responses with brain loci. Part II. Brain loci that manifested preferential activation in response to the external stimulus are deactivated. Brain locus whose deactivation selectively impairs the otherwise normal behavioral response to the external stimulus satisfies the correlation criterion. In humans, L' loci can be deactivated by means of transcranial magnetic stimulation at low frequency.

O1.4 Identifying K1 proteins. Part I. Using protein chips to identify L' locus-specific proteins in slices of tissue samples from human brain bank; using persistent stimuli to amplify mRNA transcription of K1 proteins of L loci in mice during their postnatal critical period then using subtractive hybridization to identify these proteins and their human homologues; Using databases to search for locus-specific proteins in identified brain loci.

O1.5 Identifying K1 proteins. Part II. Testing that deactivating the function of CELS proteins selectively impairs the otherwise normal behavioral response to stimuli.
  Deliver vector with P antisense fragment to L, in non-human primates
  Deliver vector with antisense gene to L, activated by taking tetracycline
  Silencing the P gene using small interfering, double stranded, RNA (siRNA)
  Create transgenic mouse with null mutation in P gene
  Use antibodies in cases that P is a cell surface receptor protein
  Deliver vector with P antisense fragment to L, in human subjects.

O1.6 Database operations. The identification procedure begins with a search of the K2 and K1 databases, and ends with updating these databases.

O2 The three levels of organization and the identification sequence. The focus of the invention is to identify the K1 protein correlates of elementary mental states, which are the lowest of the three levels of organization. The method follows a top-down approach to identifying brain loci and their K1 proteins:
  1. Modality-specific
  2. Submodality-specific
  3. Submodality elements and other elementary mental states.

O4 Each identification stage can be implemented by alternative techniques. As spelled out below, in some cases proteins are identified from human brain tissue samples, and in others, by identifying first their mouse homologues. While each technique is more appropriate in some circumstances, they are equivalent in identifying the same proteins, for which, at present, there is not alternative method.

O5 L" and L' cortical loci that remain to be identified
  O5.1 L" level exteroreceptor-related elementary mental states. The exteroreceptor-related modality-specific areas in the cerebral cortex are known. However, there is a question, which is the cortical modality-specific area for olfaction, because there are several non-contiguous olfaction-related cortical areas. The orbitofrontal cortex is the primary target for olfactory thalamic projections, and is, therefore, the modality-specific area for olfaction. Thus, of the three levels listed above, the focus is on the second and then the first level of organization and their respective K1 proteins.

O5.2 L' level—exteroreceptor-related elementary mental states. The conceptual framework redefines Brodmann areas 1 and 2 from primary to secondary sensory cortical areas. It also excludes pain from being a submodality of the somatosensory cortex (Section F6.2). Visual area V8 is provisionally taken to be the submodality-specific cortical area for color. Secondary sensory cortical areas for olfaction, taste, and pitch remain to be identified.

O5.3 L' level—Interoreceptor-related elementary mental states. Evidence indicates that the deactivation of the central nucleus of the amygdala selectively abolishes the behavioral fear response. Such an outcome satisfies our correlation criterion. The concepts and methods of the invention would be used to identify subcortical loci correlates of hunger, thirst, pleasure, pain, and other interoreceptor-related elementary mental states.

O6 Identification of K1 proteins as a diagnostic tool and as a therapeutic target. The diagnostic and therapeutic value of identifying the K1 proteins of a particular elementary mental state, such as pain, is clear.

O7 Construction of the K1 database. The systematic application of the invention culminates in completion of the K1 database.

P. Methods of Identifying Brain Loci L in Experimental Animals

P1 Considerations relating to the use of experimental animals

P1.1 The mouse as an experimental subject. The mouse may have about the same number of genes, but only about one-tenth of the brain-specific proteins, as humans. The three association areas (posterior, limbic, and anterior) are where humans differ most from non-human mammals. Additional important differences relate to perception, and some to sensations. The mouse, for example, is colorblind. But monkeys have cortical areas for color homologous to ours (Hadjikhani et al. 1998). The invention relates to identifying shared localized neural function, and then identifying CELS K1 proteins specific to these loci.

P1.2 Innateness and restricted stimulus. The environment of newborn mice should keep their responses uncontaminated by extraneous stimuli. In identifying the correlates of innate fear, for example, conditioned fear cues should be minimized, and the stimulus employed should evoke an innate response, such as abrupt loud noise or smell of cats. If the goal is to identify the correlates of basic taste, then exposure of newborn mice should be limited to one basic taste, and information about other tastes blocked. If the goal is to identify the neural correlates of the sensation of light, it is necessary to exclude elements of the stimulus related to form, depth, and movement (and also of color in experimental animals with color vision).

P1.3 Training. For stimuli types where there is normally no externally observable response, the experimental animals are trained to exhibit stimulus-recognition behavioral response. Correct recognition is reinforced by reward, such as a pellet of food, and incorrect response by punishment, such as non-damaging electric current.

P2 External stimuli for contrastive activation. An identical strain of mice is partitioned into two groups: Group A and Group B (depending on available facilities, a larger number of groups may be used). Each group is then subjected to different external stimuli. The different stimuli are within the same sensory submodality. The difference between stimuli for the two groups should be made equal to, or greater than, the JND. A brain locus that does not manifest increased metabolic, or evoked potential, activity in response to a particular external stimulus is ruled out as being directly related to that external stimulus.

P3 Identifying activated brain loci. Brain loci manifesting increased metabolic activity in response to the stimuli are identified by means of radioactively labeled glucose analog, 2-deoxyglucose (2-DG) (Sokoloff 1984). Like glucose, 2-DG is taken up by neurons manifesting increased metabolic activity. Unlike glucose, 2-DG cannot be metabolized, and it remains in the cells that ingest it. Prior to exposing the animals to these stimuli, radioactive 2-DG is injected into the afferent neurons of the sensory modality under examination (the auditory nerve, for example). The animals are scarified, and their brains are subjected to autoradiography. The 2-DG identifies brain loci that manifested increased metabolic responses. Brain loci activated in Group A, but not in Group B is designated Lj; and loci activated in Group B, but not in Group A is designated Lk.

P4 Invasive, non-destructive identification techniques.

P4.1 Voltage sensitive dyes (Cinelli 2000). Voltage sensitive dyes show activation gradients in the brain. This technique would be used in experimental animals such as the monkey for identification of K1 proteins for functions not found in the mouse, such as color vision.

P4.2 Direct stimulus. The access to the brain involved in the use of voltage sensitive dyes would then be used for the application of direct stimulation of the brain loci that manifested increased metabolic activity. A brain locus that is activated in response to external stimuli is not correlated with the behavioral response, if its direct stimulation does not produce such response. Example: The somatosensory cortex is activated by external pain stimulus that elicits pain behavioral response. But direct stimulation of the somatosensory cortex does not elicit pain response. Conclusion: The somato-sensory cortex is not directly correlated with pain.

P5 Identifying brain locus whose inactivation selectively abolishes response R.

P5.1 Training animals to manifest behavioral response to external stimulus. A new set of animals is partitioned into Group A and Group B. Group A is trained to exhibit behavioral response Rj to stimulus Sj; and Group B is trained to exhibit response Rk to stimulus Sk.

P5.2 Selective deactivation. A brain locus identified as activated in response to the particular external stimulus is then deactivated. The inactivation technique may consist of local surgical lesion, local application of neurotoxin (in non-human primates reversible deactivation would be used, such as local application of lidocaine.

P5.3 Post-deactivation test. Group A mice, with brain loci deactivation in stage O5.2, are then presented with the external stimulus Sj, that normally is followed in them by behavioral response Rj. Lj is that brain locus whose inactivation selectively abolishes behavioral response Rj. Animals in Group B are then subjected to external stimulus Sk. Rk is that brain locus whose deactivation selectively abolishes behavioral response Rk.

Q. Methods for Identifying P and P' in the Mouse

Q1 Outline of the identification of P and P'proteins by use of experimental animals.
1. Selectively amplify mRNA transcription of K1 proteins
2. Using subtractive hybridization, isolate amplified mRNA/cDNA of K1 proteins.
3. Deactivate function of P by delivering antisense fragments to L brain loci.

Q2 Contrastive amplification of mRNA transcription. Mice in their postnatal critical stage would be partitioned into Group A and Group B. Group A is then subjected to persistent stimulus Sj; and Group B is subjected to persistent stimulus Sk.

Q3 Subtractive hybridization to isolate P' and P cDNAs. The protein specificity of brain locus L in Group A is Qj=Pj+P'+P0, and in Group B is Qk=Pk+P'+P0. Tissue samples are taken from Lj, Lk, and an area of L" outside L'. The mRNA from these samples is extracted, and then converted into cDNA using reverse transcription CPR. Taking cDNA samples from L' (Lj or Lk), and from outside L', and using subtractive hybridization would result in cDNAs found in both samples, the P0 cDNAs, to hybridize. The P0 cDNAs is removed. The, Lj and Lk samples are subjected to subtractive hybridization. P' cDNAs, that that is common to both, would hybridize. These P' cDNAs are then separated using agarose gel electro-phoresis, and visualized, by stains such as ethidium bromide. The resulting bands of cDNA are extracted from the gel using recovery columns or phenol/chloroform extraction. These cDNA are then cloned and sequenced. The above procedure used to identify P' is then used to identify Pj cDNAs and Pk cDNAs, which remain unhybridized in the stage that P' was isolated.

Q4 Alternative techniques for preventing the function of P. The initial embodiment utilizes P antisense to inactivate its function. Where P is a cell surface receptor, it may be inactivated by antagonist ligand (e.g. naloxone, for some receptors in nucleus accumbens), or by monoclonal antibodies (e.g. drug Herceptin, the breast cancer drug). Some lipid vectors can pass through the cell membrane. Packaging antibodies in such a lipid vector could be used where P is intracellular. P genes can also be reversibly silenced. In all cases that P inactivation is the result of the interference with the synthesis of P, the effect is delayed until existing, functional P proteins are degraded during protein turnover. Eliminating the function of P by site-directed mutagenesis would be primarily used for drug development and gene therapy, rather than for identification.

Q5 Inhibiting the translation of P mRNA by means of antisense fragments. The initial technique of inactivating the function of P involves the delivery into L of P antisense fragments, thus impairing or inhibiting the synthesis of P proteins. This technique has undergone rapid development recently in connection with its potential use in gene therapy. A protocol similar to the one developed by Demenix et al. (2000) would be used.

Q6 Inactivation of Pj, to confirm that behavioral response Rj is selectively impaired. The delivery of any P' antisense cDNA common to columns in the submodality-specific area L' would impair or suppress the R' response. The delivery of any P antisense cDNA to L would selectively impair or suppress only the corresponding R response. For example, if the delivery of antisense cDNA to column L in the submodality-specific area for basic taste results in the suppression of only a single type of R response (such as response to a sweet taste stimulus), then the antisense cDNA is the complementary of a P protein unique to sweetness. If, however, the effect is the suppression of R1, R2, R3, R4, and R5 responses—loss of sense of taste to all taste responses—then the antisense suppresses the synthesis of a P' protein common to all columns that evoke taste in the gustatory cortex. After Pj cDNA is isolated and sequenced, antisense fragments are constructed and introduced in vivo into L. The antisense vector would impair Pj synthesis, and after a period of protein turnover, this would inactivate brain locus Lj. The inactivation of Lj, in turn, would abolish behavioral response Rj to an external stimulus. The identification of Pj is confirmed if the delivery of vector with Pj antisense to Lj impairs the behavioral response Rj, but not any related behavioral response Rk.

Q7 Down-regulation and inactivation. Once identification of CELS proteins has been confirmed, the techniques where inactivation is an end-point of down-regulation can then be used to down-regulate activity for therapeutic purposes.

R. Identifying CNS Correlates of Elementary Mental States in Human Subjects

R1 Overview. With time, an increasing number of K1 proteins would be in the K2 database of CELS proteins in the brain. After periodic update of K2 database, it would be searched for the brain locus of interest and its correlated K1 proteins. If not found in the database, L loci would be identified by non-invasive brain imaging. K1 mRNA in L loci would then be identified from brain tissue slices. In cases when the specific tissues are not available, their mouse homologue would be identified first. Confirmation of the identification of K1 proteins by their deactivation would be made first in animals. The deactivation would be accomplished by using methods such as vectors with antisense fragments, or by the reversible activation of ligand-regulated expression of an antisense gene, using ligands such as tetracycline.

R2 Using non-invasive methods to identify some L' loci in human subjects.

R2.1 Cortical L' areas. First, secondary sensory cortical areas for olfaction and taste would be identified by use of non-invasive brain imaging of activated areas between the primary sensory cortical areas and the posterior association areas. Next, L' loci within the secondary sensory areas would be identified by their preferential activation to external stimuli corresponding to different submodality elements within that submodality. For example, there are several tonotopic maps in the secondary auditory cortex. The tonotopic map specific to pitch is a secondary auditory sensory area that satisfies the identification criterion: It would manifest preferential activation in response to monaural stimuli of air vibration corresponding to any particular pitch. The direct electrical stimulus of that area would elicit the auditory sensation of simple pitch. Finally, the inactivation of any part of that tonotopic map would produce deafness to the corresponding part of the pitch range. Using non-invasive brain imaging would identify areas between the primary sensory area and the posterior association areas as secondary sensory cortical areas. Similarly, the submodality-specific area for basic tastes would be identified within the gustatory cortex, by detecting loci preferentially activated in response to stimulus consisting of one elementary taste-producing substance, such as sugar or salt.

R2.2 Subcortical L' areas. The identification criterion of selective inactivation needs to be systematically applied to various subcortical loci known to be associated with subjective states. The central nucleus of the amygdala, for example, has been associated with the basic emotion of innate fear. This needs to be confirmed by finding whether its inactivation selectively abolishes the innate fear behavioral response.

R3 Identifying CELS proteins in human subjects directly. Human K1 proteins would be identified from tissue samples of brain locus L, either directly, or from their mRNA expression.

R3.1 The direct identification of proteins. Direct identification would be performed on tissue samples from a brain bank (such as Harvard Brain Bank). Proteins would be separated by use of 2D gel electrophoresis, and identified by means of mass spectroscopy (Klose 1999).

R3.2 Identifying proteins through their mRNA expression. K1 proteins of cortical columns of secondary modality-specific areas would be identified from their mRNA expression in brain tissue samples obtained from stillborn or aborted fetuses. The modality-specific differentiation of the cerebral cortex takes place during the third trimester. Column-specific proteins would be identified by subtractive hybridization of third trimester tissue samples from second trimester tissue samples. Low abundance proteins would be more effectively identified using the high selectivity of antibodies, by techniques such as phage display (Kay et al. 1996), or aptamers (Hermann and Patel 2000).

R4 Four sources of identified K1 proteins. The identified K1 proteins would come from several different sources: Those identified in the K2 database; those identified directly from human brain tissue samples; those identified from fetal mRNA; and those identified from the model animal. These would include a percentage of false positives.

R5 The selective impairment of behavioral response R' by deactivating P'. The introduction of P' antisense fragments into L' would abolish the function of brain loci L', and selectively abolish behavioral response R'. For example, where P' is a protein common to the eight types of columns in visual area V5, its inactivation would result in akinetopsia, or motion blindness. Light touch, a sensory submodality represented by Brodmann area 1, has just a single member. Therefore P'=P. Transgenic animals with dysfunctional P will manifest no behavioral response to stimuli of light touch on the surface of their bodies.

R6 Updating the K2 and K1 databases. K2 and K1 databases would be regularly updated with newly identified K1 proteins.

S. Conclusions, Ramifications, and Scope of the Invention

S1 The conceptual framework applies to cellular function in general. For example, one problem related to extended weightlessness is the loss of muscle and bone tissue. NASA is experimenting with centrifuiges—a sub-optimal solution—to address this problem. Information about gravitation (and about the orientation of the body in space—the vestibular sense) is a result of transduction by distal sensory receptors, and is, therefore, contingent, rather than necessary (Section G2). Thus, proximate causes of the response of the cells to gravitation can be identified and provided in the absence of gravitation.

S2 The conceptual framework shifts the causal locus of neural function from intercellular to intracellular. What applies to function also applies to dysfunction: Intercellular manifestations of neuronal diseases are symptoms—inhibiting them would not constitute a cure. Consider, for example, Alzheimer's disease. It is characterized by intercellular accumulation of plaque. The March issue of *Technology Review* (Garber 2001) reports that neuroscientists currently presume that the cause of Alzheimer's is its intercellular manifestation. As such, they are developing beta-secretase inhibitors to combat these manifestations. But if the cause of Alzheimer's were intracellular, then combating its intercellular manifestation would not constitute a cure. Similar analysis applies to migraine. Migraines, which in the past were considered to be of vascular origin, are now considered to be due to intercellular function of neurotransmitters. There is no question that neurotransmitters play a role. But both the origin and the target of neurotransmitters are intracellular events. In both Alzheimer's as well as migraine, an effective drug would affect the intracellular cause of the dysfunction, as, for example, by modifying transcriptional regulation.

S3 Perception and cognition involve pattern generation and recognition. Columns in the anterior inferotemporal cortex that are specific to basic visual forms (Fujita 1992) involve pattern generation and recognition mechanisms. Identifying their molecular correlates, as well as those of columns in Brodmann area 39, which are related to the innate sense for numbers (Dehaene 1997) would complement the present focus on interconnectivity and interactivity in the study of perception and cognition.

S4 The conceptual framework makes it possible to determine homology between the neural correlates of elementary mental states of humans and other species (and in turn, to identify the evolutionary stage at which a given elementary mental state emerged), facilitating the development of psychogenic drugs by testing them first on experimental animals.

S5 It takes a fraction of a second between the presentation of an external stimulus and the resulting mental state. In addition, the number of pitch elements indicates that K1 proteins must meet a certain diversity requirement. This twin characteristic of K1 proteins excludes most protein types in the cell. If an attribute is found that sets K1 proteins apart from other CELS proteins in the brain, then the K1 database can be extracted from the K2 database under program control.

S6 In order to facilitate explanation of the invention, the examples given are of sensory elements. As it would be evident to those skilled in neuroscience and molecular biology, the concepts and methods apply equally to elementary mental states related to subcortical areas.

S7 Consider the task of identifying the K1 protein correlates of pain. For the tabula rasa neuroscientist, pain is conveyed to the CNS from the PNS, while a neuroscientist that subscribes to the computer model of the brain would deny that pain, as any other mental state, can possibly have unique neuroanatomic correlates. These two entrenched misconceptions explain, in part, the absence of effective pain medication. The methods provided by the invention apply to pain as to any other elementary mental state. The identified loci and their locus-specific proteins provide highly focused targets for modulation. Combined with available techniques of psychophysics, neuroscience, and molecular biology, it would improve the efficacy of developed drugs, while reducing their side effects.

S8 A conceptual note regarding regulating elementary mental states by modulating the function of K1 proteins: Products engineered by human beings typically have a control element that can be turned up or down. Regulation in living organisms, in contrast, involves a double control system. The faucet, for example, is provided for the regulation of the water level in a bathtub. A biological system, in contrast, would typically provide, in addition, regulation of the water outflow. Consequently, water level can be maintained near a given set-point by either controlling water inflow, outflow, or both. This fact makes it possible to modulate K1 proteins by action on either part of the control system.

APPENDIX

A Review of Five Indirectly Related Basic Issues

1. General, non-specific consciousness and attention. Elementary mental states, perception, and cognition, may be viewed as foreground events against general, non-specific background consciousness (Chalmers 2001). Background consciousness, like ambient light, has gradations from mania to depression, sleep, anesthesia and coma. In addition, there are mechanisms that serially shift the focus attention, and heightened conscious activity, among brain loci. Background consciousness and attention are necessary for awareness of foreground events, which some call the specific contents of consciousness. In contrast, a foreground event, like tasting sweet or seeing red can be selectively inactivated. Background consciousness is innate, is evoked in the CNS, and has no more basic constituents. It therefore satisfies the criterion of an elementary mental state. Satisfying the conjunction of the conditions for background consciousness, attention, and foreground mental state constitute the sufficient condition for consciousness.

2. Sensory awareness without activation of the anterior association cortex. The conceptual framework implies that sensations are evoked in secondary sensory cortical areas. Some neuroscientists have assumed that the anterior association cortex must also be activated for these mental states to be experienced. Recent experiments, however, have demonstrated that this is not the case. During rapid eye movement (REM) dreams, for example, the limbic system and secondary sensory cortical areas are activated, but the anterior association cortex is not. Moreover, the primary sensory cortical areas also remain inactive (Braun et al. 1998).

3. Ultimately, all observation is made from the first-person perspective. Observations of a person may be partitioned into those that are consistent with observations of others, and those that are not. Both types of observations are private, and thus subjective. The intersubjectively consistent observations are called "objective," the other, "subjective." Thus, first-person perspective underlies, and has epistemological priority over, third-person perspective.

4. The mind is not an emergent property of brain function. Physicalism inverts the epistemological priority of the first- and third-person perspectives. This inversion leads to the conclusion that mental events are an emergent property of brain function. For example, some scientists, who recognize that color is evoked in the brain, have been led to conclude that it does not exist outside the brain (Martin 1991), and that the world was colorless for billions of years until brains evolved (Stapp 1993). The mind is not an emergent property of brain function, and it cannot be "reduced" to the physical. The identification of physical correlates of mental states is a preliminary stage towards formulation of the findings in terms of first-person perspective.

5. Teleology and feedback mechanisms in the cell, body, and brain.

5.1 Homeostatic maintenance of thermodynamic disequilibrium in the cell. Rosenblueth, Wiener, and Bieglow (1943) have shown that explaining biological and artificial systems in teleological, goal-oriented, or feedback mechanisms is consistent with physics. Teleological explanations are not only legitimate but also necessary. Life of a cell is often characterized in terms of it being far from thermodynamic equilibrium. But so is a rock on a mountaintop. However, only the cell, while it is alive, has negative and positive feedback mechanisms (stabilization and amplification respectively) to maintain, and within limits restore, this disequilibrium. Consider the membrane potential of a living cell. The inside is electrically negative relative to the outside. The cell maintains this imbalance in a steady state (called "the resting potential") by actively transporting ions against their gradients. After disruption of the membrane potential in the neuron, it is restored within about a millisecond.

5.2 Teleological mechanisms and brain function. Some teleological mechanisms, such as the immune system, are specific to multicellular organisms, underscoring the fact that health and disease are intrinsically normative. Teleological mechanisms are central to accounting for brain function. One of the set-points homeostatically maintained by the hypothalamus, for example, is the glucose level in the blood. This regulation is not conscious when automatic, but evokes hunger when voluntary action is needed. Similarly, thermoregulation in mammals is not conscious while temperature homeostasis can be maintained automatically, but the mental state of being cold is evoked when a voluntary action is called for. The teleologic aspects of pleasure and pain, for example, are self-evident.

What is claimed is:

1. A method for identifying brain loci of neural correlates of a particular elementary mental state, such as any innate submodality element of sensation, comprising the steps of:
    (1) establishing correspondence between said submodality element of sensation and the external stimulus that normally elicits it, and then with a voluntary behavioral response, thus establish correspondence between said stimulus and said response, so that said behavioral response following said stimulus signifies the presence of the said element of sensation, and the absence of said behavioral response signifies the absence of said element of sensation;
    (2) detecting, immediately following said external stimulus and said corresponding behavioral response, brain loci that manifest transient increased activation;
    (3) identifying, among the said brain loci that manifested increased, activation in response to said stimulus, those whose inactivation selectively eliminates said behavioral response to said external stimulus, without eliminating behavioral responses to external stimuli that induce other elements of sensation within the same submodality.

* * * * *